United States Patent [19]

Kobayashi et al.

[11] 4,266,019
[45] May 5, 1981

[54] SILVER HALIDE PHOTOGRAPHIC MATERIAL CONTAINING YELLOW COUPLER

[75] Inventors: Hidetoshi Kobayashi; Mitsugu Tanaka, both of Minami-ashigara; Kozo Inouye, Odawara; Hideki Naito, Minami-ashigara, all of Japan

[73] Assignee: Fuji Photo Film Co., Ltd., Minami-ashigara, Japan

[21] Appl. No.: 74,945

[22] Filed: Sep. 13, 1979

[30] Foreign Application Priority Data

Sep. 13, 1978 [JP] Japan .................................. 53/112618

[51] Int. Cl.³ .............................................. G03C 1/40
[52] U.S. Cl. .................................... 430/551; 430/372; 430/389; 430/557; 430/558
[58] Field of Search ............... 430/556, 557, 558, 388, 430/389, 372, 551

[56] References Cited

U.S. PATENT DOCUMENTS

| | | | |
|---|---|---|---|
| 3,551,155 | 12/1970 | Yoshida et al. | 430/556 |
| 3,576,636 | 4/1971 | Matsui et al. | 439/556 |
| 3,832,386 | 8/1974 | Inoue et al. | 430/556 |
| 3,892,576 | 7/1975 | Van Poucke et al. | 430/556 |
| 4,046,575 | 9/1977 | Boie et al. | 430/557 |
| 4,057,432 | 11/1977 | Fujiwhara et al. | 430/558 |
| 4,072,525 | 2/1978 | Inouye et al. | 430/557 |

*Primary Examiner*—J. Travis Brown
*Attorney, Agent, or Firm*—Sughrue, Rothwell, Mion, Zinn and Macpeak

[57] ABSTRACT

A silver halide color photographic material containing a yellow coupler represented by following general formula (I):

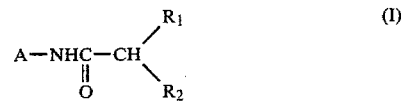

wherein A represents a yellow coupler from which one hydrogen atom bound to a carbon atom other than at a coupling active site is removed, and $R_1$ and $R_2$ each represents a straight chain or branched alkyl group containing 2 to 16 carbon atoms, with the sum of the carbon atoms contained in $R_1$ and $R_2$ being 10 to 20 is disclosed.

7 Claims, No Drawings

SILVER HALIDE PHOTOGRAPHIC MATERIAL CONTAINING YELLOW COUPLER

BACKGROUND OF THE INVENTION

1. Field of Invention

This invention relates to yellow couplers which provide, upon coupling reaction with the oxidation product of a primary amine developing agent, a dye having an extremely excellent fastness.

2. Description of the Prior Art

In the field of color light-sensitive materials, it has been eagerly desired to keep images in a developed state over a long period of time. To enhance fastness of a dye formed from a coupler is the most fundamental approach to this object. Unlike cyan couplers and magenta couplers, yellow couplers do not provide a dye having improved fastness even when used together with so-called anti-fading agents, but rather provide deteriorated fastness. Therefore, with respect to yellow couplers it has been particularly desired to enhance fastness of the dye formed from the couplers.

Japanese Patent Publication No. 16,058/74 and U.S. Pat. No. 3,892,576 disclose couplers having a structure which might be considered analogous to that of the yellow couplers of the present invention represented by formula (I) below.

The former discloses pyrazolone magenta couplers having a

moiety where $R_1$ and $R_2$ represent alkyl groups. The invention disclosed therein is directed to reducing the amount of solvent required to incorporate the couplers into a color photographic emulsion and improve the spectral absorption characteristics of color images by utilizing the high solubility of the couplers for high boiling organic solvents and differs from the present invention in construction and object. In addition, yellow couplers show a different behavior from magenta couplers in terms of their photographic properties, and while magenta couplers having a

moiety show a high solubility for high boiling organic solvents, it is extremely difficult to predict that yellow couplers having such a moiety would provide extremely fast dyes.

U.S. Pat. No. 3,892,576 discloses introducing a

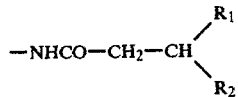

moiety into photographic additives to increase their diffusion resistance.

SUMMARY OF THE INVENTION

A principal object of the present invention is to provide yellow couplers which provide, by coupling reaction, a dye having good light fastness without sacrificing other photographic properties to attain this object.

In addition to the above-described light fastness, the couplers of the present invention show an excellent solubility for high-boiling organic solvents and an excellent coloring property.

The novel couplers of the present invention are represented by formula (I);

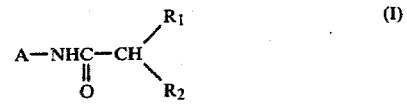

wherein A represents yellow coupler nucleus from which one hydrogen atom bound to a carbon atom other than at the coupling active position is removed, and $R_1$ and $R_2$ each represents a straight or branched alkyl group containing 2 to 16 carbon atoms, with the sum of the carbon atoms contained in $R_1$ and $R_2$ being 10 to 20.

Preferably A represents a pivaloylacetanilide coupler nucleus, a benzoylacetanilide coupler nucleus, a malondiamide coupler nucleus, a benzothiazolylacetanilide coupler nucleus, a benzothiazolylacetate coupler nucleus, a benzoxazolylacetamide coupler nucleus, a benzoxazolyacetate coupler nucleus, a benzimidazolylacetamide coupler nucleus, a benzimidazolylacetate coupler nucleus, and those derived from hetero cyclic-substituted acetamides and hetero cyclic-substituted acetates, where such heterocyclic-ring substituent can be a 5-, 6- or 7-membered ring which can contain more than one hetero atom such as a nitrogen atom, an oxygen atom and sulfur atom, included in U.S. Pat. No. 3,841,880.

Particularly useful groups represented by A are those derived from the compounds represented by following general formula (II);

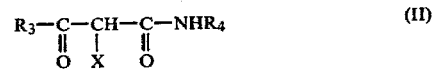

wherein $R_3$ represents an aliphatic group, an aromatic group, or a hetero cyclic group, and $R_4$ represents an aromatic group or a hetero cyclic group and X is defined as below.

In the above formula, the aliphatic group such as an alkyl group, an alkenyl group, an aralkyl group, an alkoxyalkyl group, an aryloxyalkyl group, etc., represented by $R_3$ preferably contains 1 to 22 carbon atoms, and may be substituted, unsubstituted, straight, branched or cyclic and is preferably an alkyl group. Preferable substituents for the alkyl group include an alkoxy group, an aryloxy group, an amino group, an acylamino group, etc. which themselves may further be substituted. Specific examples of useful aliphatic group represented by $R_3$ are; isopropyl, isobutyl, tert-butyl, isoamyl, tert-amyl, 1,1-dimethylbutyl, 1,1-dimethylhexyl, 1,1-diethylhexyl, dodecyl, hexadecyl, octadecyl, cyclohexyl, 2-methoxyisopropyl, 2-phenoxyisopropyl, 2-p-tert-butylphenoxyisopropyl, α-aminoisopropyl, α-(diethylamino)isopropyl, α-(succinimido)isopropyl, α-

(phthalimido) isopropyl, α-(benzenesulfonamido)isopropyl, etc.

Where $R_3$ or $R_4$ represents an aromatic group such as a phenyl group, a naphtyl group, etc. in particular a phenyl group and the aromatic group may be substituted. An aromatic group such as a phenyl group may be substituted by a group having up to 32 carbon atoms such as an alkyl group, an alkenyl group, an alkoxy group, an alkoxycarbonyl group, an aliphatic amido group, an alkylsulfamoyl group, an alkylsulfonamido group, an alkylureido group, an alkyl-substituted succinimido group, etc. The alkyl substituent may contain in its chain an aromatic group such as a phenylene group. The phenyl group may also be substituted by a group having 6 to 32 carbon atoms such as an aryloxy group, an aryloxycarbonyl group, an arylcarbamoyl group, an arylamido group, an arylsulfamoyl group, an arylsulfonamido group, an arylureido group, etc. The aryl moiety of these substituents may be further substituted by one or more alkyl groups containing a total of 1 to 22 carbon atoms.

Furthermore, the phenyl group represented by $R_3$ or $R_4$ may be substituted by an amino group including a lower alkyl-substituted amino group containing 1 to 6 carbon atoms, a hydroxy group, a carboxy group, a sulfo group, a nitro group, a cyano group, a thiocyano group, or a halogen atom.

Still further, $R_3$ or $R_4$ may represent a substituent wherein a phenyl group is condensed with a saturated or unsaturated ring, which may contain hetero atoms, for example, a naphthyl group, a quinolyl group, an isoquinolyl group, a chromanyl group, a coumaranyl group, a tetrahydronaphthyl group, etc. These substituents themselves may have a substituent or substituents.

Where $R_3$ or $R_4$ represents a 5- or 6-membered heterocyclic group containing more than one hetero atom such as a nitrogen atom, an oxygen atom and a sulfur atom, which may be saturated, unsaturated or aromatic, the hetero cyclic group is bound to the carbon atom of the carbonyl group of the acyl group or to the nitrogen atom of the amido group in the α-acylacetamido group via one of the ring-forming carbon atoms. Examples of such heterocyclic rings include thiophene, furan, pyran, pyrrole, pyrazole, pyridine, pyrazine, pyrimidine, pyridazine, indolizine, imidazole, thiazole, oxazole, triazine, oxazine, etc. These may further have a substituent or substituents on the ring.

X in formula II represents a group represented by the formulae (III), (IV), or (V).

 (III)

 (IV)

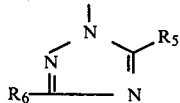 (V)

In general formula (III), Z represents the non-metallic atoms, which may contain an oxygen group or a sulfur group, necessary for forming a 4-, 5- or 6-membered ring, which may be saturated or unsaturated, together with

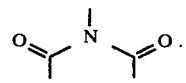

Suitable examples of the ring represented by general formula (III) are shown as follows

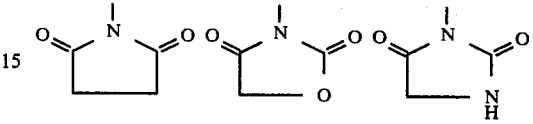

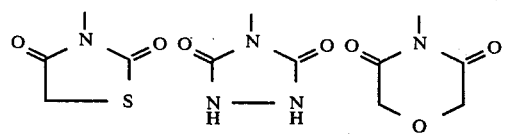

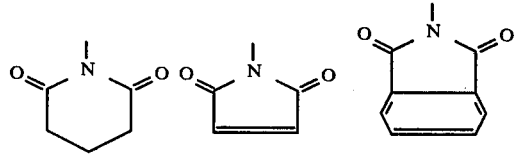

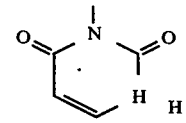

In general formula, (IV), R represents a monocyclic aryl group such as a phenyl group having 6 to 30 carbon atoms, which may be unsubstituted or substituted by a group such as —SO$_2$CH$_3$, —COOH or —CN, for example

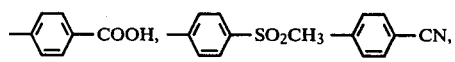

4-carboxy phenyl, 4-methanesulfonyl phenyl, 4-cyanophenyl, etc.; or a 5- or 6-membered hetero cyclic group containing more than one hetero atom such as a nitrogen atom, an oxygen atom or a sulfur atoms which may be saturated or unsaturated, such as pyrazole, triazole, tetrazole, etc. In general formula (V), $R_5$ and $R_6$ each represents a hydrogen atom, a halogen atom, a carboxylic acid ester group, the carboxylic acid of which contains 1 to 18 carbon atoms and may be selected from an aliphatic acid group and, as an ester group, a methyl group, an ethyl group, an octyl group, etc.; an amino group, an alkyl group having 1 to 18 carbon atoms, which may be straight chain, branched or cyclic, an alkylthio group having 1 to 18 carbon atoms, in which the alkyl moiety may be straight chain, branched or cyclic, an alkoxy group having 1 to 18 carbon atoms, in which the alkyl moiety may be straight chain, branched or cyclic, an alkylsulfoxy group having 1 to 18 carbon atoms, in which the alkyl moiety may be straight chain, branched or cyclic, a carboxy group, a sulfoxy group, a phenyl group, which may be substituted by a chlorine atom, a methoxy group, a methyl group etc., or a hetero cyclic ring group such as a pyridino group.

Of these, the moieties represented by the formula (VI) to (IX) of the formula (III) are preferred.

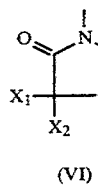 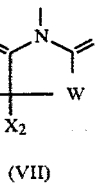 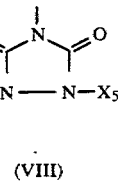

(VI)    (VII)    (VIII)

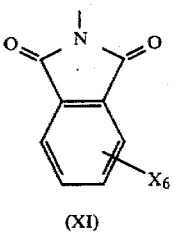

(XI)

In these formulae, $X_1$ and $X_2$ each represents a hydrogen atom, an alkyl group having 1 to 18 carbon atoms, which may be straight chain or branched, a monocyclic aryl group having 6 to 20 carbon atoms, an alkoxy group having 1 to 18 carbon atoms, which may be straight chain, branched or cyclic, a monocyclic aryloxy group having 6 to 18 carbon atoms, or a hydroxy group $X_3$, $X_4$ and $X_5$ each represents a hydrogen atom, an alkyl group having 1 to 18 carbon atoms, which may be straight chain or branched, a monocyclic aryl group having 6 to 18 carbon atoms, a monocyclic aralkyl group having 7 to 20 carbon atoms, or an acyl group having 1 to 18 carbon atoms, which may be an aliphatic group or an aromatic group, W represents an oxygen atom or a sulfur atom, $X_6$ represents a monovalent substituent such as a hydrogen atom, a halogen atom, a nitro group, a cyano group, a thiocyano group, a hydroxyl group, an alkoxy group, an aryloxy group, an acyloxy group, an alkyl group having 1 to 18 carbon atoms, which may be straight chain or branched, an alkenyl group having 1 to 18 carbon atoms, which may be straight chain or branched, a monocyclic aryl group having 6 to 20 carbon atoms, an amino group, a carboxy group, an acyl group, an alkoxycarbonyl group having 1 to 18 carbon atoms, an aryloxycarbonyl group having 6 to 28 carbon atoms, a charbamoyl group having 1 to 18 carbon atoms, an acylamino group, which may be an aliphatic acylamino group having 2 to 18 carbon atoms or an aromatic acylamino group having 7 to 29 carbon atoms, an imido group, a sulfo group, an alkylsulfonyl group having 1 to 18 carbon atoms, an arylsulfonyl group having 6 to 28 carbon atoms, an alkoxysulfonyl group having 1 to 18 carbon atoms, an aryloxysulfonyl group having 6 to 28 carbon atoms, a sulfamoyl group, a sulfonamido group, an ureido group, a thioureido group, or the like.

A preferred class of couplers within the present invention can be represented by the formula (X):

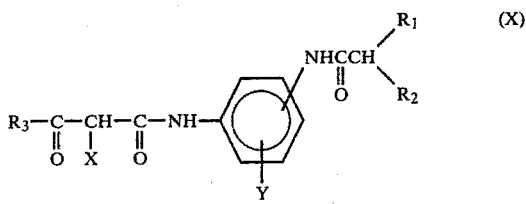

where $R_1$, $R_2$, $R_3$ and X are defined as in formula (II) and Y is preferably a halogen atom or an alkoxy group.

Example of compounds of the present invention are as follows.

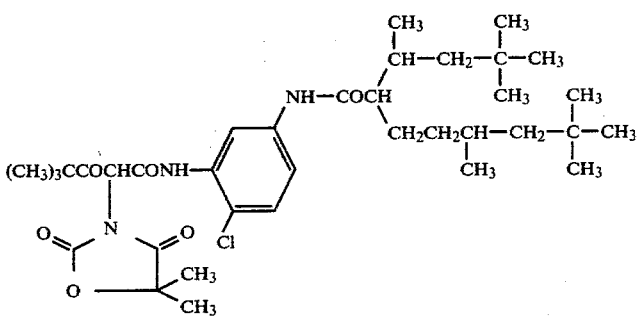

1.

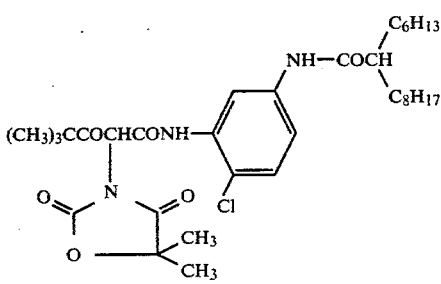

2.

-continued
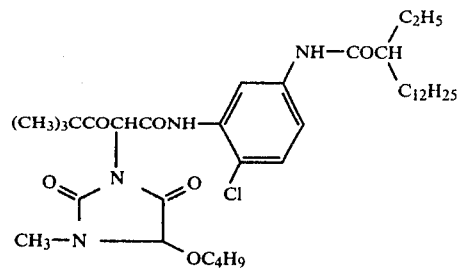 3.
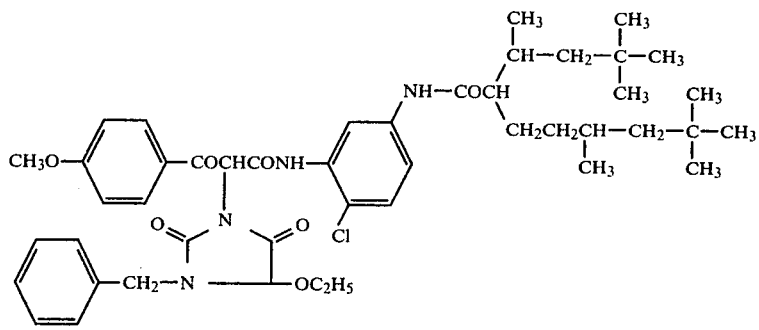 4.
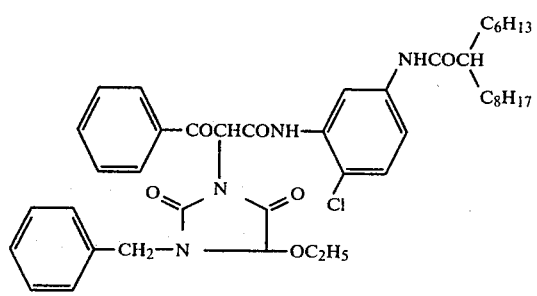 5.
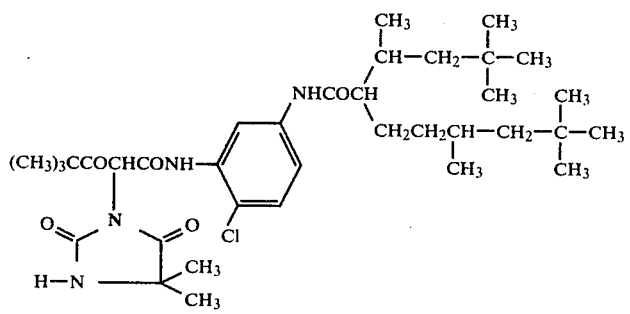 6.
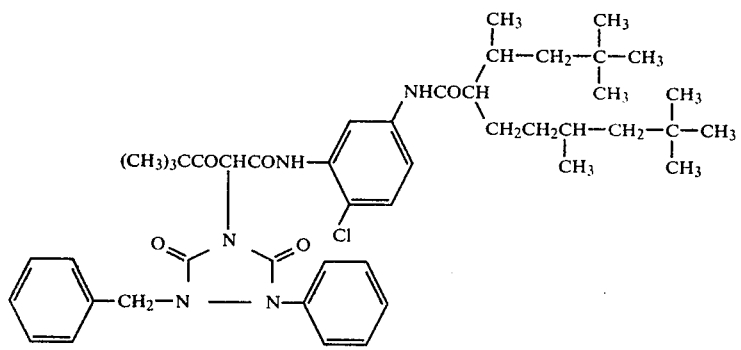 7.

-continued
8.
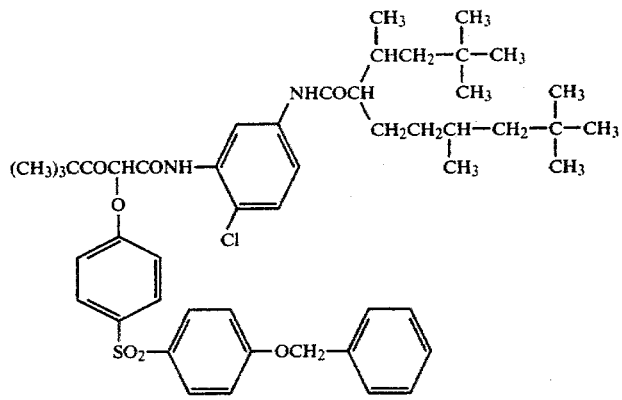
9.
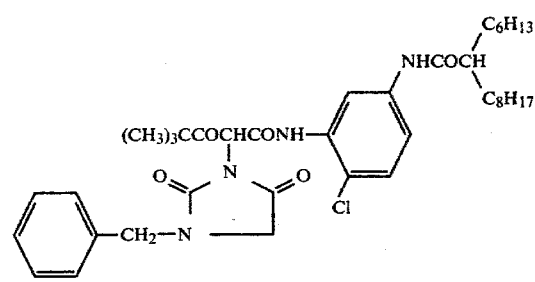
10.
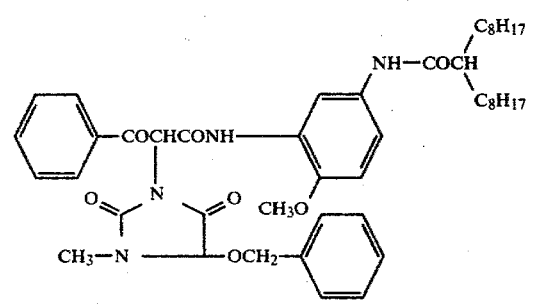
11.
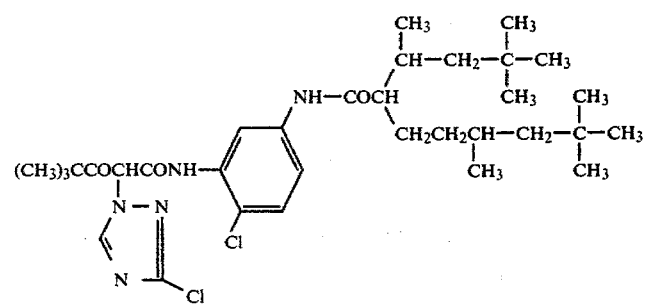
12.
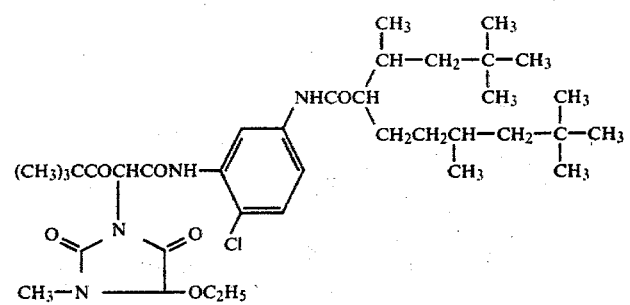

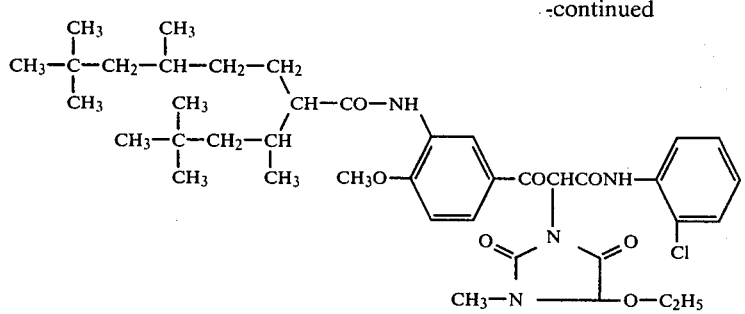

Of the compounds of the present invention, compound 1 illustration above is particularly preferable.

The couplers of the present invention can be synthesized according to the following reaction scheme.

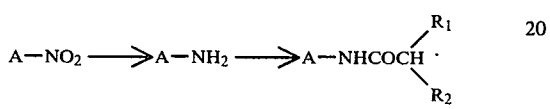

In the above formulae, A has the same meaning as defined in general formula (I).

SYNTHESIS EXAMPLE 1

Synthesis of
α-pivaloyl-α-(5,5-dimethyl-2,4-dioxo-3-oxazolidinyl)-2-chloro-5-[2-(1,3,3-trimethylbutyl)-5,7,7-trimethyloctanamido]-acetanilide (coupler 1):

α-pivaloyl-α-(5,5-dimethyl-2,4-dioxo-3-oxazolidinyl)-2-chloro-5-nitroacetanilide was refluxed with iron in aqueous isopropyl alcohol in the presence of ammonium chloride as a catalyst for 1 hour to obtain a reduced product, α-pivaloyl-α-(5,5-dimethyl-2,4-dioxo-3-oxazolidinyl)-5-amino-2-chloroacetanilide. An acid chloride obtained by the reaction between 2-(1,3,3-trimethylbutyl)-5,7,7-trimethyloctanoic acid and thionyl chloride was refluxed with an equimolar amount of α-pivaloyl-α-(5,5-dimethyl-2,4-dioxo-3-oxazolidinyl)-5-amino-2-chloroacetanilide in acetonitrile for 3 hours. After acetonitrile was distilled off from the resulting condensation product, the oily matter thus obtained was dissolved in chloroform and washed with water. After chloroform was distilled off, recrystallization of the residue from n-hexane afforded the desired coupler having a melting point of 105° to 107° C. in a yield of 75%.

| Elemental Analysis: | H | C | N |
| --- | --- | --- | --- |
| Calcd.: | 8.52 | 65.28 | 6.34 |
| Found: | 8.42 | 65.33 | 6.24 |

SYNTHESIS EXAMPLE 2

Synthesis of
α-pivaloyl-α-(5,5-dimethyl-2,4-dioxo-3-oxazolidinyl)-2-chloro-5-(2-hexyldecanamido)acetanilide (coupler 2):

An acid chloride obtained by the reaction between 2-hexyldecanoic acid and thionyl chloride was refluxed with an equimolar amount of α-pivaloyl-α-(5,5-dimethyl-2,4-dioxo-3-oxazolidinyl)-5-amino-2-chloroacetanilide obtained according to Snythesis Example 1 in acetonitrile for 3 hours. After acetonitrile was distilled off from the resulting condensation product, the oily matter thus obtained was dissolved in chloroform and washed with water. After chloroform was distilled off, recrystallization of the residue from n-hexane afforded the desired coupler having a melting point of 117° to 120° C. in a yield of 70%.

| Elemental Analysis: | H | C | N |
| --- | --- | --- | --- |
| Calcd.: | 8.26 | 64.38 | 6.62 |
| Found: | 8.22 | 64.25 | 6.54 |

In the production of silver halide color photographic light-sensitive materials, the couplers of the present invention may be used alone or in combination.

In the color photographic light-sensitive material containing the coupler of the present invention may be incorporated, for example, DIR couplers or DIR compounds (e.g., those described in U.S. Pat. Nos. 3,632,345, 3,227,554, 3,379,529, Japanese Patent Application (OPI) Nos. 122335/74, 34232/75, 135310/75, etc.), yellow dye-forming couplers (e.g., those described in West German Patent Application (OLS) No. 2,213,461, U.S. Pat. Nos. 3,510,306, 3,644,498, 3,894,875, etc.) magenta dye-forming couplers (e.g., those described in U.S. Pat. No. 3,615,506, West German Patent Application (OLS) Nos. 2,418,959, 2,424,467, etc.), or cyan dye-forming couplers (e.g., those described in U.S. Pat. Nos. 2,474,293, 3,034,892, 3,591,383, 3,311,476, 3,476,563, etc.).

The coupler of the present invention is advantageously dispersed in a photographic emulsion in a solution of an organic solvent. A specific example of dispersing couplers is described in detail in U.S. Pat. No. 3,676,131. The organic solvents useful for dissolving the couplers are those which are slightly soluble in water and have a high boiler point (about 160° C.); for example, substituted hydrocarbons, carboxylic acid esters, benzoic acid esters, citric acid esters, carboxylic acid amides, phosphoric acid esters, ethers, etc. Specific examples thereof include di-n-butyl phthalate, n-octylbenzoate, o-acetyl tributyl citrate, tricresyl phosphate, tri-n-hexyl phosphate, N,N-diethyl-caprylamide, etc. It is advantageous to use low-boiling auxiliary solvents in addition to these high-boiling solvents. Examples of such solvents include propylene carbonate, ethyl acetate, butyl acetate, cyclohexanol, tetrahydrofuran, cyclohexanone, etc.

The use of a surface active agent is advantageous for finely dispersing these solvents in a hydrophilic colloid to be used as a photographic emulsion. Diffusion-resistant couplers containing in one molecule thereof both a ballast group and a carboxylic or sulfonic acid group are soluble in a neutral or alkaline aqueous solution, and the solution can be added to the photographic emulsion.

The couplers are generally added to an emulsion in an amount of about 5 to 1500 g per mol of silver halide. However, the amount can vary depending upon the use, with about 10 to 500 g per mol of silver halide being preferable. A suitable amount of a silver halide is about 0.2 to 4 g/m$^2$ and preferably about 0.5 to 3 g/m$^2$.

The couplers of the present invention can be applied to various color light-sensitive materials as well as various silver halide light-sensitive materials such as color negative films, color positive films, color reversal films, color paper, etc. and are preferably located in a silver halide emulsion layer.

Suitable silver halide emulsions which can be used in the present invention include those containing silver chloride and silver bromide as well as mixed halides of silver, such as silver chlorobromide, silver iodobromide, silver chloroiodobromide, etc.

The silver halide grains of these emulsions may be of a cubic form, an octahedral form, or may have a mixed crystalline structure.

The silver halide grain size distribution may be narrow or broad, and is not particularly limited. Suitable methods of preparing the silver halide emulsion which can be used include those well known in the art, such as the single and double jet process, the controlled double jet process, etc.

Two or more types of silver halide emulsions which have been prepared separately using different processes can be employed. The grain structure of the silver halide may be uniform or different from the surface to the interior, or may be of the so-called "conversion" type as described in British Pat. No. 635,841, and U.S. Pat. No. 3,622,318.

Further, silver halide grains which provide latent images primarily at the surface thereof or in the interior can be employed in the present invention.

The silver halide emulsions used in this invention may be chemically sensitized using well-known chemical sensitizers including N,N,N'-trimethylthiourea, the complex salts of monovalent gold such as the thiocyanates or the thiosulfates, etc., stannous chloride, hexamethylenetetramine.

Suitable hydrophilic high molecular weight materials which can be present in the photographic coatings of the present invention include gelatin, cellulose derivatives, such as carboxymethylcellulose, hydroxyethylcellulose, etc., carbohydrate derivatives, such as strach derivatives, snythetic hydrophilic colloid materials, such as poly(vinyl alcohol), poly(N-vinyl-pyrrolidone), copolymers containing acrylic acid, polyacrylamide and the derivatives or partially hydrolyzed products of the above-described polymers, etc. Of these, the most representative is gelatin and gelatin is most generally used. The gelatin can be partly or completely replaced by a synthetic polymer or a gelatin derivative.

The couplers of the present invention are applicable to multi-layer color light-sensitive materials (e.g., those described in U.S. Pat. Nos. 3,726,681, 3,516,831, British Pat. Nos. 818,687, 923,045, etc.) or to the process described in British Pat. No. 1,513,321. Furthermore, they can be used together with DIR compounds described in West German Patent Application (OLS) No. 2,322,165 or U.S. Pat. No. 3,703,375).

The light-sensitive material to be used for the present invention may contain, in an emulsion layer or a neighboring layer, a p-substituted phenol derivative such as a hydroquinone derivative, which is advantageous for stabilizing color images. Particularly effective p-substituted phenol derivatives such as 6,6'-Dihydroxy-4,4,7,4',4',7'-hexamethyl-2,2'-bis-spirochromane are those described in U.S. Pat. Nos. 2,360,290, 3,418,613, 2,675,314, 2,710,801, 2,728,659, 2,732,300, 2,735,765, 2,816,028, 3,609,262, 3,432,300, 3,457,079, 3,573,050, 3,574,627, 3,764,337, etc. Japanese Patent Publication No. 13496/68, Japanese Patent Application (OPI) No. 4738/72.

The light-sensitive material containing the coupler of the present invention may contain in an emulsion layer or a neighboring layer an ultraviolet absorbing agent such as 2-(2-hydroxy-3,5-di-tert-amylphenyl)benzotriazole described in, for example U.S. Pat. Nos. 3,250,617, 3,253,921, etc. for stablization of images.

The couplers of the present invention can also be applied to low-silver content light-sensitive materials containing approximately ½ to 1/100 the silver in conventional emulsions. With such color light-sensitive materials containing a reduced amount of silver halide, adequate image densities can be obtained according to, for example, image-forming processes for increasing the amount of dye produced utilizing color intensification with peroxide, cobalt complexes, or sodium chlorite (described in, for example, West German Patent Application (OLS) No. 2,357,694, U.S. Pat. Nos. 3,674,490, 3,761,265, 4,002,477, 3,970,458, 3,923,511, 3,856,524, 3,862,842, 3,826,652, 3,834,907, 3,765,891, West German Patent Application (OLS) Nos. 2,044,833, 2,056,359, 2,056,360, 2,226,770, etc.

The color photographic material of the present invention can be subjected to conventional and well known processings comprising, after exposure, color development, bleaching and fixing. Each processing step may be combined with another using a processing agent capable of accomplishing the corresponding functions. A typical example of such a combined processing is a mono-bath process using a blix.

Depending on the requirements, the development processing can include additional steps such as prehardening, neutralization, primary development (black-and-white development), image stabilization, washing with water, etc. The processing temperature, which is determined depending on the kind of photographic material as well as by the processing composition, is sometimes below about 18° C. but, in most cases, is not lower than 18° C.

A particularly useful temperature range is from about 20° to 60° C. The temperature may be varied from one processing step to another in the processing.

A color developer comprises an aqueous alkaline solution with a pH not lower than about 8, and more preferably between 9 and 12, containing a color developing agent the oxidation product of which is capable of reacting with a coupler to form a dye.

Suitable color developing agents which can be used include, for example, 4-amine-N,N-diethylaniline, 3-methyl-4- amino-N,N-diethylaniline, 4-amino-N-ethyl-N-β-hydroxyethylaniline, 3-methyl-4-amino-N-ethyl-N-β-hydroxyethylaniline, 4-amino-3-methyl-N- ethyl-N-β-methanesulfamidoethylaniline, 4-amino-N,N-dimethylaniline, 4- amino-3-methoxy-N,N-diethylaniline, 4-amino-3-methyl-N-ethyl-N-β- methoxyethylaniline, 4-amino-3methoxy-N-ethyl-N-β-methoxyethylaniline, 4-amino-3-β-methanesulfamidoethyl-N,N-diethylaniline, and the salts thereof, such as the sulfates, the hydrochlorides, the sulfites, the p-toluenesulfonates, etc.

Other color developing agents which can be used are described in U.S. Pat. Nos. 2,592,364 and 2,193,015, Japanese Patent Application (OPI) No. 64933/73, L.E.A. Mason, *Photographic Processing Chemistry*, pp 226–229, Focal Press, London (1966), etc.

Each of the above-described compounds can be used in conjunction with 3-pyrazolidone derivatives. Further, a number of additives well-known in the art may be present in the color developer.

The coupler of this invention can also be incorporated into the color developer and a suitable amount of the coupler of this invention which can be used in the color developing solution is about 0.5 to 20 g per liter of the developing solution.

The photographic material of the present invention is subjected to bleaching after color development. This step may be combined with fixing, whereby the processing solution contains a fixing agent in addition to a bleaching agent.

Suitable bleaching agents include ferricyanide salts, bichromate salts, water-soluble cobalt (III) salts, water-soluble copper (II) salts, water-soluble quinones, nitrosophenol, polyvalent metal compounds containing Fe(III), Co(III), Cu(II), with complex salts of such metals with organic acids, such as, for example, ethylenediamine tetraacetic acid, nitrilotriacetic acid, imidoacetic acid, N-hydroxyethylethylenediaminetriacetic acid and other aminopolycarboxylic acids, malonic acid, tartaric acid, malic acid, diglycolic acid, dithioglycolic acid and 2,6-dipicolic acid copper complex salt, etc., being particularly preferred, peracids, such as alkyl peracids, persulfates, permanganates, hydrogen peroxide, etc., hypochlorites, etc.

Other additives, such as bleach accelerating agents as disclosed in U.S. Pat. Nos. 3,042,520 and 3,241,966, Japanese Patent Publication Nos. 8506/70 and 8836/70, etc., can be further added to the bleaching solution.

The present invention will be explained in more detail by reference to the following example.

EXAMPLE

A solution prepared by heating 27 g of the aforesaid Coupler (1) and as coupler solvents 13.5 ml of dioctyl-butyl phosphate and 50 ml of ethyl acetate at 70° C. was added to 300 ml of an aqueous solution containing 50 g of gelatin and 2.0 g of sodium dodecylbenzenesulfonate, and stirred, followed by preheating and passing five times through a colloid mill, Thus, the coupler was finely emulsified and dispersed together with the solvents.

The whole of the resulting emulsion dispersion was added to 1.0 kg of a photographic emulsion containing 54 g of silver bromoiodide and 60 g of gelatin and, after the addition of 30 ml of a 5% acetone solution of triethylene phosphamide as a hardener, the pH of the resulting mixture was adjusted to 6.0, followed by coating it on a cellulose triacetate film base in a dry thickness of 7.0 μ to obtain sample A.

In a manner analogous to the above procedure except for using 27 g each of Coupler (2), Coupler (11), Comparative Coupler (A), and Comparative Coupler (B) in place of abovedescribed Coupler (1), there were obtained samples B, C, D and E.

These films were subjected to stepwise exposure for sensitometry, then to the following processings:

| Color Developing Steps: | | | |
|---|---|---|---|
| 1. | Color development processing | 30° C. | 4 min. |
| 2. | Bleach-fixing | 30° C. | 2 min. |
| 3. | Washing | 30° C. | 2 min. |
| 4. | Stabilizing bath | 30° C. | 2 min. |

Each of the processing solutions used in the color development steps is as follows.

| Color Developer: | |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (sulfate) | 0.02 g |
| Sodium Hydroxide | 4 g |
| Benzyl Alcohol | 15.8 ml |
| Diethylene Glycol | 20 ml |
| 4-(N-Ethyl-N-β-methanesulfonamido-ethyl)amino-2-methylaniline sesquisulfate | 8 g |
| Water to make | 1 liter (pH:10.2) |

| Bleach-Fixing Solution: | |
|---|---|
| Iron(II) Ethylenediaminetetraacetate | 45 g |
| Ammonium Thiocyanate | 10 % |
| Sodium Sulfite | 10 g |
| Ammonium Thiosulfate (60% by weight aqueous solution) | 100 ml |
| Sodium Ethylenediaminetetraacetate | 5 g |
| Water to make | 5 liter (pH: 6.9) |

| Stabilizing Bath: | |
|---|---|
| Tartaric Acid | 10 g |
| Zinc Sulfate | 10 g |
| Sodium Metaborate | 20 g |
| Water to make | 1 liter |

The thus obtained developed films were subjected to the tests for stability to light. Samples were placed in a xenon testing apparatus to expose to $2.5 \times 10^6$ lux·hr light for 8 days. Then, the percentage of reduction in color density of the light-exposed samples and of the in exposed samples were compared.

Table 1 shows the results of the measurement of percentages of reduction in color density of color images at initial densities of 0.50 and 1.50.

Comparative Coupler (A) and (B) have the following structural formulae, respectively.

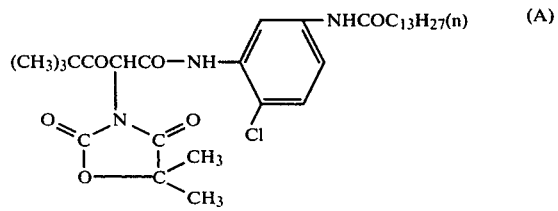
(A)

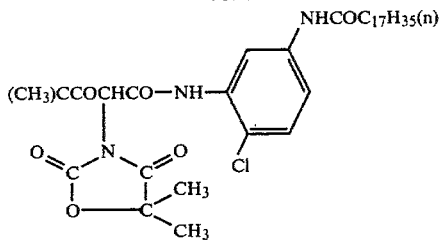

(B)

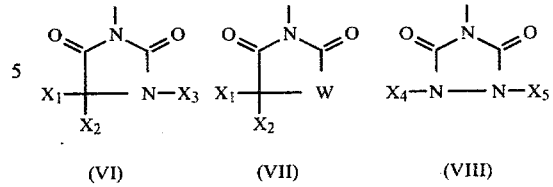

(VI) (VII) (VIII)

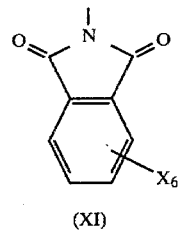

(XI)

TABLE 1

| Sample | Coupler | Percentage of Reduction in color Density | |
|---|---|---|---|
| | | Initial Density 0.5 | Initial Density 1.5 |
| A | (1) | 18 | 15 |
| B | (2) | 27 | 21 |
| C | (11) | 19 | 17 |
| D | A | 50 | 43 |
| E | B | 51 | 41 |

As is clear from the results in Table 1, Samples A, B, and C using the compounds of the present invention suffered less fading with light as compared with comparative samples D and E.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material containing a yellow coupler represented by following general formula (I);

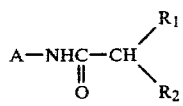

(I)

wherein A represents a yellow coupler from which one hydrogen atom bound to a carbon atom other than at a coupling active site is removed having the formula (II);

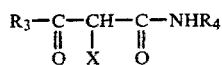

(II)

wherein $R_3$ represents an aliphatic group, an aromatic group or a heterocyclic ring, $R_4$ represents an aromatic group or a heterocyclic ring, wherein X is represented by the formulae (VI)–(IX);

wherein $X_1$ and $X_2$ each represents a hydrogen atom, an alkyl group, an aryl group, an alkoxy group, an aryloxy group, or a hydroxy group, $X_3$, $X_4$ and $X_5$ each represents a hydrogen atom, an alkyl group, an aryl group, an aralkyl group or an acyl group, W represents an oxygen atom or a sulfur atom and $X_6$ represents a monovalent substituent, and $R_1$ and $R_2$ each represents a straight chain or branched alkyl group containing 2 to 16 carbon atoms, with the sum of the carbon atoms contained in $R_1$ and $R_2$ being 10 to 20.

2. The silver halide color photographic material of claim 1, wherein said coupler is represented by the formulae

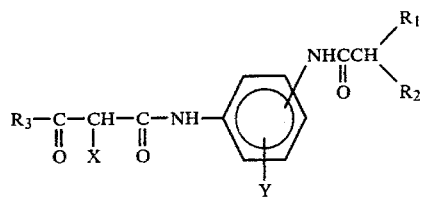

wherein $R_1$, $R_2$, $R_3$ and X are defined as above and Y represents a halogen atom or an alkoxy group.

3. The color photographic material of claims 1 or 2, wherein said coupler is present in an amount of about 5 to 1500 grams per mol of silver halide.

4. The color photographic material of claims 1 or 2, wherein said coupler is present in an amount of about 10 to 500 grams per mol of silver halide.

5. The color photographic material of claim 1, wherein said material is a color negative film, a color positive film, a color reversal film or a color paper.

6. The color photographic material of claim 1, wherein said coupler is located in a silver halide emulsion layer.

7. The color photographic material of claim 6, wherein said silver halide emulsion layer or an adjacent layer contains a p-substituted phenol derivative.

* * * * *